United States Patent
Moon et al.

(10) Patent No.: US 10,005,800 B2
(45) Date of Patent: Jun. 26, 2018

(54) MIXED METAL HALIDE PEROVSKITE COMPOUND AND SEMICONDUCTOR DEVICE INCLUDING THE SAME

(71) Applicant: KOREA RESEARCH INSTITUTE OF CHEMICAL TECHNOLOGY, Daejeon (KR)

(72) Inventors: Sang Jin Moon, Daejeon (KR); Jong Cheol Lee, Daejeon (KR); Ki Jeong Kong, Daejeon (KR); Won Wook So, Daejeon (KR); Won Suk Shin, Daejeon (KR); Sang Kyu Lee, Daejeon (KR); Bo Keun Park, Daejeon (KR); Muhammad Jahandar, Daejeon (KR); Chang Eun Song, Busan (KR)

(73) Assignee: KOREA RESEARCH INSTITUTE OF CHEMICAL TECHNOLOGY, Daejeon (KR)

(*) Notice: Subject to any disclaimer, the term of this patent is extended or adjusted under 35 U.S.C. 154(b) by 199 days.

(21) Appl. No.: 15/057,571

(22) Filed: Mar. 1, 2016

(65) Prior Publication Data
US 2016/0268510 A1 Sep. 15, 2016

(30) Foreign Application Priority Data
Mar. 12, 2015 (KR) .................. 10-2015-0034669

(51) Int. Cl.
| | | |
|---|---|---|
| C22C 11/02 | (2006.01) | |
| C22C 11/04 | (2006.01) | |
| C01F 7/00 | (2006.01) | |
| C07F 7/22 | (2006.01) | |
| H01L 51/42 | (2006.01) | |
| C07F 13/00 | (2006.01) | |
| C07F 7/24 | (2006.01) | |

(52) U.S. Cl.
CPC .................. *C07F 7/22* (2013.01); *C07F 7/24* (2013.01); *C07F 13/00* (2013.01); *H01L 51/424* (2013.01); *Y02E 10/549* (2013.01)

(58) Field of Classification Search
CPC ........... C22C 11/02; C22C 11/04; C01F 7/005
See application file for complete search history.

(56) References Cited

U.S. PATENT DOCUMENTS 9,508,884 B2* 11/2016 Wenham .................. C25D 3/60
2015/0144195 A1* 5/2015 Irwin .................. H01G 9/2027
136/260

FOREIGN PATENT DOCUMENTS

KR 1020140007045 A 1/2014

OTHER PUBLICATIONS

Julian Burschka, et al., "Sequential deposition as a route to high-performance perovskite-sensitized solar cells", Nature, vol. 499, Jul. 18, 2013; pp. 316-320.
Mingzhen Liu, et al; "Efficient planar heterojunction perovskite solar cells by vapour deposition", Nature, vol. 501, Sep. 19, 2013; pp. 395-402.

(Continued)

*Primary Examiner* — Magali P Slawski
(74) *Attorney, Agent, or Firm* — Ladas & Parry LLP; Loren K. Thompson (57) ABSTRACT

Provided are a mixed metal halide perovskite compound, and an electronic device including the same, wherein the mixed metal halide perovskite compound includes an organic cation, two or more kinds of metal cations, and a halogen anion.

5 Claims, 7 Drawing Sheets

(56) References Cited

OTHER PUBLICATIONS

Samuel D. Stranks, et al; "Electron-Hole Diffusion Lengths Exceeding 1 Micrometer in an Organometal Trihalide Perovskite Absorber", Science, vol. 342, Oct. 16, 2013, pp. 341-344.
Shuangyong Sun, et al: "The origin of high efficiency in low-temperature solution-processable bilayer organometal halide hybrid solar cells", Energy & Environmental Science, vol. 7, pp. 399-407 ; First published online Oct. 23, 2013.
Koren Office Action dated Feb. 4, 2016; Appln. No. 10-2015-0034669.

\* cited by examiner

MIXED METAL HALIDE PEROVSKITE COMPOUND AND SEMICONDUCTOR DEVICE INCLUDING THE SAME

CROSS-REFERENCE TO RELATED APPLICATIONS

This application claims priority under 35 U.S.C. § 119 to Korean Patent Application No. 10-2015-0034669, filed on Mar. 12, 2015, in the Korean Intellectual Property Office, the disclosure of which is incorporated herein by reference in its entirety.

TECHNICAL FIELD

The following disclosure relates to a mixed metal halide perovskite compound and a semiconductor device including the same.

BACKGROUND

Recently, an organic solar cell using organic-inorganic hybrid materials such as organometallic halide as photoactive materials has received attention. In 2013, Professor Grachel's team (Switzerland) announced a solar cell having the same structure as a solid-state dye-sensitized solar cell but replacing existing organic dye only with an organometallic perovskite compound ($CH_3NH_3PbI_3$) [Nature, 499, 316 (2013)]. Further, Professor Snaith (Oxford University, England) found that when some of iodine (I) is replaced with chlorine (Cl) in the same organometallic perovskite compound ($CH_3NH_3PbI_3$), mobility of charges largely increased [Science, 342, 341 (2013)]. Accordingly, it was found that a cell having a similar structure to a multi-layer organic thin-film solar cell could be manufactured by replacing a porous $TiO_2$ film which is an essential electron transport layer of the solid-state dye-sensitized solar cell with an $Al_2O_3$ scaffolder layer [Science, 338, 643 (2012)] or by removing the porous $TiO_2$ film [Nature, 501, 395 (2013), Energy & Environ. Sci., DOI:10.1039/C3EE43161D (2013)].

From these recent results, the organometallic perovskite compound is possible to manufacture a simple thin-film structured device similar to other inorganic thin film solar cell, while simultaneously maintaining advantages of a low-temperature wet manufacturing process of the existing solid-state dye-sensitized solar cells or the existing organic thin-film solar cells.

However, the organometallic perovskite compound is based on a halogen element unlike other common oxide perovskite compound, such that it is difficult to completely remove instability of the metal halide itself according to hygroscopic property.

In addition, currently, the organometallic perovskite compound has a methyl ammonium ($CH_3NH_3^+$) organic ligand having the smallest molecular size and having an iodine (I) group having the largest atomic radius as main components, and even though the organometallic perovskite compound has a three-dimensional cubic perovskite structure, a light absorption range is the maximum of 800 nm, which is narrow, such that it is not possible to be changed into a molecular structure where a wider wavelength is absorbed.

RELATED ART DOCUMENT (Non-Patent Document 1) Nature, 499, 316 (2013)
(Non-Patent Document 2) Science, 342, 341 (2013)
(Non-Patent Document 3) Nature, 501, 395 (2013)
(Non-Patent Document 4) Energy & Environ. Sci., DOI: 10.1039/C3EE43161D (2013)

SUMMARY

An embodiment of the present invention is directed to providing an organic mixed metal halide perovskite compound (mixed organometal halide having a perovskite structure) capable of having excellent photoelectric conversion efficiency and a thin film characteristic and absorbing light at a wider wavelength range, and an electronic device including the same.

In one general aspect, there is provided a mixed metal halide perovskite compound represented by Chemical Formula 1 below:

$$AM^1_xM^2_yX_3 \quad \text{Chemical Formula 1}$$

in Chemical Formula 1, A is a monovalent organic cation, $M^1$ is a first metal cation selected from Pb or Sn, $M^2$ is a second metal cation including at least one selected from Cu and Mn, X is one or two or more kinds of halogen anions selected from F, Cl, Br and I, a molar ratio of $M^1$ and $M^2$ satisfies x+y=1, and x is a real number of 0.9 to 0.98.

In addition, when $M^2$ is a mixture of Cu and Mn, each content of Cu and Mn may be a real number of 0.001 to 0.099, and the sum of contents of Cu and Mn may have a molar ratio of 0.02 to 0.1.

In the mixed metal halide perovskite compound according to an exemplary embodiment of the present invention, the organic cation contained in the mixed metal halide perovskite compound may be the monovalent organic cation, and the monovalent organic cation may be at least one selected from alkyl ammonium, aralkyl ammonium and heterocyclic ammonium, but the present invention is not limited thereto.

Specifically, the monovalent organic cation may be at least one selected from C1-C24 alkyl ammonium, C6-C24 aralkyl ammonium, and heterocyclic ammonium including N, S, or O-based element of C4-C24 or two or more elements thereof, but the present invention is not limited thereto.

Here, alkyl may be C1-C24 linear or branched alkyl, specifically, C1-C12 linear or branched alkyl. More specifically, the alkyl may be C1-C6 linear alkyl. As an example, the alkyl may be methyl, ethyl, propyl, butyl, pentyl or hexyl. More specifically, the alkyl may be methyl.

Here, aralkyl may be aralkyl including at least one C6-C24 phenyl ring. As an example, the aralkyl may be phenylalkyl, naphthylalkyl, anthracenylalkyl, tetracenylalkyl, or pentacenylalkyl, and specifically, phenylalkyl or naphthylalkyl, and more specifically, phenylmethyl ($C_6H_5CH_2$—).

Here, heterocyclic may include at least one heterocyclic ring including N, S, or O-based element of C4-C24 or two or more elements thereof. As an example, the heterocyclic ring means pyrrole, pyridine, indole, furan, thiophene, thiozole, benzothiozole or benzodithiophene, and specifically, thiophene, a benzothiozole or benzodithiophene, and more specifically, a thiophene ($C_4H_4S$—) group, etc.

Specifically, in the mixed metal halide perovskite compound of the present invention, two or more kinds of metal cation including the first metal cation and the second metal cation in Chemical Formula 1 may be selected from i) to v) below:
  i) Pb and Mn,
  ii) Pb and Cu, iii) Sn and Mn,
iv) Sn and Cu, and
v) Pb, Mn and Cu.

In the mixed metal halide perovskite compound according to an exemplary embodiment of the present invention, the halogen anion may include bromine ions and iodine ions.

In another general aspect, there is provided a photoelectric conversion device including the mixed metal halide perovskite compound as described above.

The photoelectric conversion device according to an exemplary embodiment of the present invention may include a transparent electrode, a first charge transport layer formed on the transparent electrode, a photoactive layer formed on the first charge transport layer and containing the mixed metal halide perovskite compound, a second charge transport layer formed on the photoactive layer, and a counter electrode formed on the second charge transport layer.

DETAILED DESCRIPTION OF EMBODIMENTS

Hereinafter, a mixed metal (complex) halide perovskite compound and an electronic device including the same according to the present invention will be described in detail with reference to the accompanying drawings. The drawings to be described below are provided by way of example so that the idea of the present invention can be sufficiently transferred to those skilled in the art to which the present invention pertains. Therefore, the present invention may be implemented in many different forms, without being limited to the drawings to be described below. The drawings below may be exaggerated in order to specify the spirit of the present invention. Here, unless technical and scientific terms used herein are defined otherwise, they have meanings understood by those skilled in the art to which the present invention pertains. Description of known functions and components that may obscure the gist of the present invention will be omitted from the following description and the accompanying drawings.

The present inventors developed an organometallic mixed metal halide perovskite compound having more excellent photoelectric characteristics as compared to the existing organometallic perovskite-based compounds utilized for various electronic devices such as transistors, photodiodes, sensors, photoelectric conversion devices, etc., and completed the present invention.

The mixed metal halide perovskite compound according to the present invention may be represented by Chemical Structure 1 below:

$$AM^1_x M^2_y X_3 \qquad \text{Chemical Formula 1}$$

in Chemical Formula 1, A is a monovalent organic cation, $M^1$ is a first metal cation selected from Pb or Sn, $M^2$ is a second metal cation including at least one selected from Cu and Mn, X is one or two or more kinds of halogen anions selected from F, Cl, Br and I, x+y=1, x is a real number of 0.9 to 0.98, and y is a real number of 0.02 to 0.1. In addition, when $M^2$ is a mixture of Cu and Mn, Chemical Formula 1 may be represented by Chemical Formula 2 of $AM^1_x Cu_{y1} Mn_{y2} X_3$. In Chemical Formula 2, y1 and y2 may be each independently a real number of 0.001 to 0.099, the sum of y1+y2 may be a real number of 0.02 to 0.1, x may be a real number of 0.9 to 0.98, and x+(y1+y2)=1. In Chemical Formula 2, A, $M^1$ and X are the same as defined in Chemical Formula 1.

In the mixed metal halide perovskite compound according to an exemplary embodiment of the present invention, the two or more kinds of mixed metal cations may be regularly or irregularly (randomly) dispersed and positioned in the above-described mixed metal halide perovskite structure, and the two or more kinds of halogen anions may be regularly or irregularly (randomly) dispersed and positioned at a position of X in the above-described mixed metal halide perovskite structure.

The organometallic mixed metal perovskite compound according to an exemplary embodiment of the present invention may have more excellent photoelectric conversion efficiency as compared to the existing perovskite-based compounds.

In addition, as compared to an organic single metal halide perovskite compound, a perovskite structure may be formed with stability and reproducibility while having more excellent photoelectric conversion efficiency and a different effect in that light is capable of being absorbed at a wide wavelength range.

In the mixed metal halide perovskite compound of the present invention, two or more kinds of metal cation including the first metal cation and the second metal cation may be selected from i) to v) below:
i) Pb and Mn,
ii) Pb and Cu,
iii) Sn and Mn,
iv) Sn and Cu, and
v) Pb, Mn and Cu.

That is, in the mixed metal halide perovskite compound according to an exemplary embodiment of the present invention, the first metal cation may be Pb cation or Sn cation, and the second metal cation may be Mn, Cu, or Mn and Cu. When the mixed metal halide perovskite compound is utilized as a photoactive material, Mn may remarkably increase Voc, and particularly, Cu may remarkably increase short-circuit current density.

In the mixed metal halide perovskite compound according to an exemplary embodiment of the present invention, the organic cation contained in the mixed metal halide perovskite compound may be the monovalent organic cation, and the monovalent organic cation may be at least one selected from alkyl ammonium, aralkyl ammonium and heterocyclic ammonium, but the present invention is not limited thereto.

Specifically, the monovalent organic cation may be at least one selected from C1-C24 alkyl ammonium, C6-C24 aralkyl ammonium, and heterocyclic ammonium including N, S, or O-based element of C4-C24 or two or more elements thereof, but the present invention is not limited thereto.

Here, alkyl may be C1-C24 linear or branched alkyl, specifically, C1-C12 linear or branched alkyl. More specifically, the alkyl may be C1-C6 linear alkyl. As an example, the alkyl may be methyl, ethyl, propyl, butyl, pentyl or hexyl. More specifically, the alkyl may be methyl.

Here, aralkyl may be aralkyl including at least one C6-C24 phenyl ring. As an example, the aralkyl may be phenylalkyl, naphthylalkyl, anthracenylalkyl, tetracenylalkyl, or pentacenylalkyl, and specifically, phenylalkyl or naphthylalkyl, and more specifically, phenylmethyl ($C_6H_5CH_2$—).

Here, heterocyclic may include at least one heterocyclic ring including N, S, or O-based element of C4-C24 or two or more elements thereof. As an example, the heterocyclic ring means pyrrole, pyridine, indole, furan, thiophene, thiozole, benzothiozole or benzodithiophene, and specifically, thiophene, a benzothiozole or benzodithiophene, and more specifically, a thiophene ($C_4H_4S$—) group, etc.

In the mixed metal halide perovskite compound according to an exemplary embodiment of the present invention, the halogen anion contained in the mixed metal halide perovskite compound may be one or two or more kinds of one halogen anion(s) selected from the group consisting of F, Cl, Br and I. As specific examples, the halogen anion may include I and Br. In the case where two or more kinds of halogen anions are contained in the mixed metal halide perovskite compound, when it is assumed that the total number of moles of the halogen ions contained in the in the mixed metal halide perovskite compound is 1, a first halogen ion may have 0.5 mol to 0.99 mol, and a second halogen ion different from the first halogen ion may have 0.01 mol to 0.5 mol. As specific example, the first halogen ion may be iodine (I) and the second halogen ion may be bromine (Br).

Upon representing X by Chemical Structure, X may be represented by $X^1_a X^2_b$ (wherein $X^1$ is one halogen ion selected from F, Cl, Br and I, $X^2$ is different from $X^1$ and is one halogen ion selected from F, Cl, Br and I, a is an integer of 0<a<1, b is an integer of 0<b<1, and a+b=1). Specifically, in Chemical Formulas 1 and 2, X is represented by $X^1_a X^2_b$ (wherein $X^1$ is iodine (I), $X^2$ is bromine (Br), a is an integer of $0.5 \leq a \leq 0.99$, b is an integer of $0.01 \leq b \leq 0.5$, and a+b=1).

The mixed metal halide perovskite compound according to an exemplary embodiment of the present invention may be a photoactive material that absorbs light energy to produce photoelectrons and photoholes or that absorbs electrical energy to produce light. Specifically, the mixed metal halide perovskite compound according to an exemplary embodiment of the present invention may be a light absorber of the photoelectric conversion device.

The mixed metal halide perovskite compound according to an exemplary embodiment of the present invention may be prepared by preparing a solution in which corresponding precursors are introduced into a solvent so as to satisfy the above-described composition and materials, and then simply drying the prepared solution. This preparation is performed by crystallization characteristic by self-assembly of an organometallic perovskite compound.

The present invention may include a semiconductor device including a transistor including the above-described mixed metal halide perovskite compound; or a photoelectric conversion device including a photodiode, a photoconductive sensor, a phototransistor, a solar cell, an image sensor, etc., including the above-described mixed metal halide perovskite compound.

Figure 1:
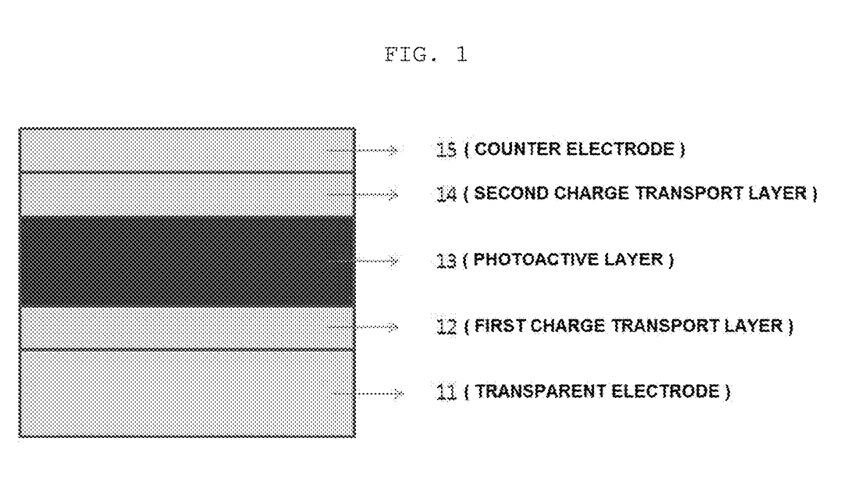
FIG. 1 is an exemplary cross-sectional view of a photoelectric conversion device provided with a mixed metal halide perovskite compound according to an exemplary embodiment of the present invention.
Figure 2:
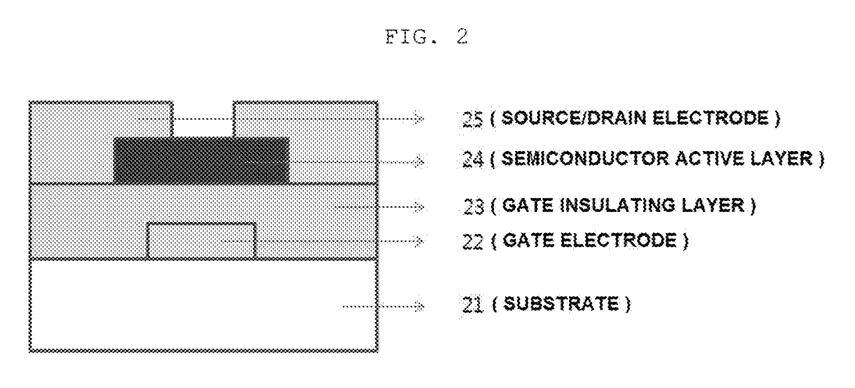
FIG. 2 is an exemplary cross-sectional view of a transistor provided with a mixed metal halide perovskite compound according to an exemplary embodiment of the present invention.

As specific examples, the present invention may include a thin-film type solar cell shown in FIG. 1 or a thin-film transistor shown in FIG. 2, but the present invention is not limited thereto. Here, in FIG. 1, a photoactive layer 13 may contain the above-described mixed metal halide perovskite compound. In FIG. 2, a semiconductor active layer 24 may contain the above-described mixed metal halide perovskite compound.

Hereinafter, the photoelectric conversion device according to an exemplary embodiment of the present invention is described in more detail, as an example of the photoelectric conversion device which is a solar cell.

FIG. 1 is a cross-sectional view of the photoelectric conversion device according to an exemplary embodiment of the present invention. As shown in FIG. 1, the photoelectric conversion device may include a conductive transparent electrode 11, a first charge transport layer 12 formed on the transparent electrode 11, a photoactive layer made of the above-described mixed metal halide perovskite compound and formed on the first charge transport layer, and a second charge transport layer 14 formed on the photoactive layer, and a counter electrode 15 formed on the second charge transport layer.

The first charge transport layer may be an electron transport layer and the second charge transport layer may be a hole transport layer. On the contrary, the first charge transport layer may be a hole transport layer and the second charge transport layer may be an electron transport layer.

Here, according to design of the photoelectric conversion device, the first charge transport layer or the second charge transport layer may not be provided. On the contrary, the first charge transport layer or the second charge transport layer may be implemented into different materials of multilayer thin-film forms. When the first charge transport layer becomes the electron transport layer, the conductive transparent electrode 11 functions as a negative electrode, and the counter electrode functions as an positive electrode, and when the first charge transport layer becomes the hole transport layer, two electrodes function conversely.

The photoactive layer, that is, a photo-absorption layer, including the above-described mixed metal halide perovskite compound may also be a single phased one layer, but the present invention is not limited thereto, and may have a form in which the mixed metal halide perovskite compound and any other semiconductor or nonconductor materials are uniformly mixed, or may have a multilayer film structure in which the mixed metal halide perovskite compound and any other semiconductor materials are formed as layers, respectively, and stacked. In addition, although it is shown that interfaces of each layer or each film are shown as planes in FIG. 1, but the present invention is not limited thereto, and a portion of interlayers adjacent to each other may have an interpenetrating three-dimensional form.

The photoelectric conversion device may be thin-film solar cell as shown in FIG. 1. Upon briefly explaining an operation principle of the thin-film solar cell by way of example, solar light incident into the solar cell device is firstly absorbed by the photoactive layer 13 containing the mixed metal halide perovskite compound to produce exciton. The exciton acts a diffusion motion in any direction, and is separated into electrons and holes in an interface or depletion layer between the charge transport layer and the photoactive layer or in the photoactive layer itself. As an example, when the first charge transport layer is 'the electron transport layer', electrons are escaped from the first charge transport layer 12 and introduced into the conductive transparent electrode 11 which is the negative electrode, and at the same time, holes are escaped from 'the hole transport layer' which is the second charge transport layer 14 and introduced into the counter electrode 15 which is the positive electrode, such that total solar cell is operated. When property of the electron transport layer is reversed to the above-described case, directions of the positive electrode and the negative electrode are reversed accordingly, but the present invention is not limited thereto.

According to an exemplary embodiment of the present invention, the conductive transparent electrode 11 may be manufactured by coating general indium doped tin oxide (ITO), fluorine doped tin oxide (FTO), aluminum doped zinc oxide (AZO), gallium doped zinc oxide (GZO), etc., on a transparent glass or plastic substrate, or may be manufactured by coating or printing one or two or more of combinations of silver nanowire (nano-silver wire), silver mesh, copper mesh, carbon nanotubes (CNT), graphene, PEDOT:PSS (poly-(3,4-ethylenedioxythiophene):polystyrene sulfonate which are relatively recently known in the art, but the present invention is not limited thereto.

The electron transport layer may include at least one selected from the group consisting of general metal oxides, that is, oxides of Zn, Ti, Sn, Si, Zr, Al, Mg, and Y and metal composite oxides thereof, organic derivatives such as LiF, Ca, C60-fullerene and C60-PCBM (phenyl-C61-butyric acid methyl ester), and organic derivatives such as C70-fullerene and C70-PCBM, polymer electrolytes such as PFN (poly-(9,9-bis(3'-(N,N-dimethylamino)propyl)-2,7-fluorene)-alt-2,7-(9,9'-dioctylfluorene)), and non-conjugation polymers such as polyethylenimine ethoxylated (PEIE), but the present invention is not limited thereto.

As a specific example, the electron transport layer may be formed by coating $TiO_2$ or ZnO on the electrode as one dense layer, but may be formed into two layers by coating a different kind of material such as C60-PCBM or C70-PCBM again on the $TiO_2$ or ZnO single layer. Here, the dense layer preferably has a thickness of 100 nm or less, and more preferably, 1 to 50 nm, and the two layers formed by coating twice, preferably has a thickness of 200 nm or less, and more preferably, 1 to 50 nm, but the present invention is not limited thereto.

As another example, the electron transport layer may be formed by coating $TiO_2$ or ZnO as described previously on the electrode as one dense single layer, and coating particle shaped $TiO_2$ or ZnO again on the dense single layer to form a porous layer, thereby forming the electron transport layer formed into two layers having different shapes, but the present invention is not limited thereto. Here, a thickness of the porous layer is preferably 1000 nm or less, for example, may be 200 to 900 nm, 300 to 900 nm, 400 to 900 nm, 500 to 900 nm, 600 to 900 nm, 200 to 800 nm, 300 to 800 nm, 400 to 800 nm, 500 to 800 nm, 300 to 700 nm, 400 to 700 nm, 500 to 700 nm, 300 to 600 nm, and 400 to 600 nm, and preferably, 300 to 600 nm, but the present invention is not limited thereto.

The photoactive layer containing the mixed metal halide perovskite compound, that is, the photo-absorption layer may be manufactured into a single phased one layer. Preferably, a thickness of the photoactive layer containing the mixed metal halide perovskite compound, that is, the photo-absorption layer, may be 1000 nm or less, and more preferably, may have a range of 200 to 800 nm, and may be 300 to 800 nm, 400 to 800 nm, 500 to 800 nm, 600 to 800 nm, 300 to 700 nm, 400 to 700 nm, 500 to 700 nm, 300 to 600 nm, 400 to 600 nm, 500 to 600 nm, 300 to 500 nm, and 400 to 500 nm according to kinds of materials, but the present invention is not limited thereto.

According to another example, with the purpose of maximizing light absorption by scattering, facilitating creation and flow of charges and improving film-forming property, the present photoactive layer may be uniformly mixed with at least any one semiconductor or nonconductor compound which is different from the composite metal halide perovskite compound selected from metal oxide semiconductors such as $TiO_2$ and ZnO, or organic semiconductors such as C60-PCBM, C70-PCBM, P3HT, PEDOT:PSS, or metal oxide nonconductors such as Si oxide, Zr oxide, Al oxide, Mg oxide, and Y oxide, or organic nonconductors such as polyethylene glycol (PEG), polyvinyl pyrrolidone (PVP), polyvinyl alcohol (PVA), polyethylene oxide (PEO) and Triton X-100, but the present invention is not limited thereto.

The hole transport layer may include at least one selected from general metal oxides such as Mo oxide, W oxide, V oxide, Ni oxide, Ru oxide, and composite metal oxides thereof, or P typed conductive polymers such as PEDOT:PSS (poly(3,4-ethylenedioxythiophene) poly(styrenesulfonate)), P3HT (poly[3-hexylthiophene]), conductive low molecules such as spiro-MeOTAD (2,2',7,7'-tetrakis(N,N-di-p-methoxyphenyl-amine)-9,9'-spirobifluorene), graphene and partially oxidized graphene, but the present invention is not limited thereto.

As an example, the hole transport layer may be formed by coating PEDOT:PSS or spiro-MeOTAD or Mo oxide on the photoactive layer as one dense layer, but may be formed into two layers by coating a different kind of material such as P3HT, Spiro-MeOTAD, Mo oxide or W oxide again on the PEDOT:PSS or spiro-MeOTAD or Mo oxide layer. Here, a thickness of the dense layer may be preferably 500 nm or less, and more preferably, may have a range of 30 to 300 nm, and may be 30 to 60 nm, 30 to 120 nm, 30 to 200 nm, 30 to 250 nm, 60 to 100 nm, 60 to 150 nm, 60 to 200 nm, 100 to 200 nm, 150 to 200 nm, and 200 to 300 nm according to kinds of materials, but the present invention is not limited thereto. The thickness of second layer of hole transport layer having two layered structure is preferably 100 nm or less, and more preferably, has a range of 10 to 50 nm, but the present invention is not limited thereto.

As another example, in order to form a hole transport layer having high conductivity, a dopant such as lithium bis(trifluoro methanesulfonyl)imide (Li-TFSI), and an additive such as tertiary butyl pyridine (tBP) may be mixed with the conductive polymer and the conductive low molecules, but the present invention is not limited thereto.

As another example, the conductive polymer such as P3HT may include at least one selected from benzothiazole-based, benzodithiophene-based, and diketopyrrolopyrrole (DPP)-based, but the present invention is not limited thereto.

The counter electrode may include one selected from Ag, Au, Al, Cu, and Ni, but the present invention is not limited thereto. Here, a thickness of the counter electrode may be preferably 500 nm or less, and for example, may be 50 to 400 nm, 100 to 400 nm, 200 to 400 nm, 300 to 400 nm, 100 to 300 nm, 200 to 300 nm, 100 to 200 nm, and preferably, 100 to 300 nm, but the present invention is not limited thereto.

A manufacturing method of the thin-film solar cell according to an exemplary embodiment of the present invention may include i) forming an electron transport layer by coating or printing an inorganic compound or organic compound on a glass or plastic substrate (for example, PET) coated with general ITO, as a conductive transparent electrode, ii) forming a photoactive layer by coating or printing a mixed metal halide perovskite compound absorbing light while contacting the electron transport layer, iii) forming a hole transport layer by coating or printing an inorganic compound or an organic compound transporting holes produced from light while contacting the photoactive layer, and iv) forming a counter electrode by coating or printing a metallic compound releasing current to the outside while contacting the hole transport layer, but the present invention is not limited thereto.

According to an exemplary embodiment of the present invention, step i) of forming of the electron transport layer by coating or printing the inorganic compound or organic compound may be performed by coating or printing a ZnO precursor solution or a paste including ZnO particulates on the ITO glass, followed by heat treatment, but the present invention is not limited thereto. Here, the coating method or the printing method may include at least one of general wet methods such as spin coating, spray coating, dip coating, doctor blading, and slot die coating method, and drying methods such as general vacuum heat deposition and sputtering method, but the present invention is not limited thereto. In addition, the heat treatment may be generally performed at a range of 100° C. to 550° C. for about 30 minutes to 1 hour in the air or vacuum or under inert atmosphere, and these conditions may vary depending on types of substrates, types of precursors, and the presence or absence of binders, but the present invention is not limited thereto.

According to another example, in step i) of forming of the electron transport layer by coating or printing the inorganic compound or organic compound, the electron transport layer may be formed into two layers by coating or printing different kind of material such as C60-PCBM again on one electron transport layer as previously formed, for example, on the dense ZnO layer, wherein the second layer may be manufactured by including at least one of general wet methods such as spin coating, spray coating, dip coating, doctor blading, and slot die coating method, and using at least one of the drying methods such as general vacuum heat deposition and sputtering method, but the present invention is not limited thereto.

Further, the heat treatment of the second layer may be generally performed at a range of 100° C. to 550° C. for about 30 minutes to 1 hour in the air or vacuum or under inert atmosphere, and these conditions may vary depending on types of substrates, types of precursors, and the presence or absence of binders, but the present invention is not limited thereto.

According to another example, in step i) of forming of the electron transport layer by coating or printing the inorganic compound or organic compound, the electron transport layer may be formed into two anisotropic layers by coating or printing a different shaped material, for example, particle shaped $TiO_2$ again on one electron transport layer as previously formed, for example, on the dense $TiO_2$ layer, such that the electron transport layer may be formed into two anisotropic layers including a first dense layer and a second porous layer, wherein the second layer second layer may also be manufactured by using at least one of general wet methods such as spin coating, spray coating, dip coating, doctor blading, and slot die coating method, but the present invention is not limited thereto. Further, the heat treatment of the second layer may be generally performed at a range of 100° C. to 550° C. for about 30 minutes to 1 hour in the air or vacuum or under inert atmosphere, and these conditions may vary depending on types of substrates, types of precursors, and the presence or absence of binders, but the present invention is not limited thereto.

According to an exemplary embodiment of the present invention, step ii) of forming of the photoactive layer by coating or printing a mixed metal halide perovskite compound absorbing light while contacting the electron transport layer may be performed by firstly dissolving the perovskite compound itself or a precursor thereof in at least one suitable polar organic solvents such as N,N-dimethyl formamide (DMF), N,N-dimethyl acetamide (DMA), dimethyl sulfoxide (DMSO), butyrolactone (BLT), acetonitrile (ACN), methanol, ethanol, etc., below degree of saturation, and repeating a process of coating or printing the solution on the electron transport layer, followed by heat treatment, but the present invention is not limited thereto.

Here, the coating method or the printing method may include at least one of general wet methods such as spin coating, spray coating, dip coating, doctor blading, slot die coating method, screen printing, and offset printing method, but the present invention is not limited thereto. As an example, the coating method may be a general vacuum heat deposition or sputtering method which is a dry method of drying the mixed metal halide perovskite compound or the precursor in solid state as it is rather than dissolving the mixed metal halide perovskite compound or the precursor in the solvents, but the present invention is not limited thereto. Further, the heat treatment may be generally performed at a range of 50° C. to 200° C. for about 10 minutes to 2 hours in the vacuum or under inert atmosphere, and these conditions may vary depending on types of substrates, and types of mixed metal halide perovskite compounds, but the present invention is not limited thereto.

According to another example, step ii) of forming of the photoactive layer by coating or printing the mixed metal halide perovskite compound absorbing light while contacting the electron transport layer may be performed by mixing the perovskite compound dissolved in the polar organic solvent as described above with at least any one semiconductor or nonconductor compound that is different from the perovskite compound and selected from metal oxide semiconductors such as $TiO_2$ and ZnO, or organic semiconductors such as C60-PCBM, C70-PCBM, P3HT, PEDOT:PSS, or metal oxide nonconductors such as Si oxide, Zr oxide, Al oxide, Mg oxide, and Y oxide, or polar compounds such as polyethylene glycol (PEG), polyvinyl pyrrolidone (PVP), polyvinyl alcohol (PVA), polyethylene oxide (PEO) and Triton X-100, thereby preparing a uniform solution or slurry, and coating or printing the solution or slurry on the electron transport layer, followed by heat treatment, but the present invention is not limited thereto. Here, the coating method or the printing method may include general wet methods such as spin coating, spray coating, dip coating, doctor blading, slot die coating method, but the present invention is not limited thereto. Further, the heat treatment may be generally performed at a range of 50° C. to 200° C. for about 10 minutes to 2 hours in the vacuum or under inert atmosphere, and these conditions may vary depending on types of substrates, and types of mixed metal halide perovskite compounds, but the present invention is not limited thereto. According to an exemplary embodiment of the present invention, step iii) of forming of the hole transport layer by coating or printing the inorganic compound or the organic compound transporting holes produced from light while contacting the photoactive layer may be performed by coating or printing a compound having excellent hole transport property, for example, Mo oxide precursor or slurry on the photoactive layer, followed by heat treatment, but the present invention is not limited thereto. Here, the coating method or the printing method may include at least one of general wet methods such as spin coating, spray coating, dip coating, doctor blading, slot die coating method, but the present invention is not limited thereto. As an example, Mo oxide solid phase as it is may be coated by general vacuum heat deposition or sputtering method, but the present invention is not limited thereto. Further, the heat treatment may be generally performed at a range of 100° C. to 200° C. for about 10 minutes to 2 hours in the vacuum or under inert atmosphere, and these conditions may vary depending on types of substrates, types of mixed metal halide perovskite compounds, and types of compounds of the hole transport layer, but the present invention is not limited thereto.

According to an exemplary embodiment of the present invention, step iv) of forming of the counter electrode by coating or printing a metallic compound releasing current to the outside while contacting the hole transport layer may be performed by coating or printing silver (Ag) paste on the hole transport layer, followed by heat treatment, but the present invention is not limited thereto. Here, the coating method or the printing method may include at least one of the general wet methods such as spin coating, spray coating, dip coating, doctor blading, slot die coating method, screen printing, and offset printing method, but the present invention is not limited thereto. As an example, the coating method may be performed by general vacuum heat deposition or sputtering method using silver particles or target, but the present invention is not limited thereto. In addition, the heat treatment may be generally performed at a range of 100° C. to 200° C. for about minutes to 2 hours in the vacuum or under inert atmosphere, but the present invention is not limited thereto.

Hereinafter, the present invention is described in more detail on the basis of Examples below. However, the present invention is not limited to these Examples.

EXAMPLE 1

$CH_3NH_3I$ (191 mg) was dissolved in a mixed solvent of gamma butyrolactone (BTL) and dimethyl sulfoxide (DMSO) (volume ratio=6/4) (1 CC) to prepare a solution having about 1.2 molar concentration.

In addition, to a separate mixed solvent of BTL and DMSO (volume ratio=6/4) (1 CC), lead iodide ($PbI_2$) (539.4 mg) and manganese iodide ($MnI_2$) (9.3 mg) were dissolved to thereby prepare a mixed metal iodide solution (metal precursor solution) in which a molar ratio between Pb and Mn is 97.5:2.5 (Compound No. 1-1 in Table 1).

Compound Nos. 1-2 to 1-5 in Table 1 were prepared by performing the same method as Compound No. 1-1, except for changing the material of the metal precursor to be mixed and the relative molar ratio between the metal precursors. In detail, Compound No. 1-2 in Table 1 was prepared by mixing $PbI_2$ (525.5 mg) with $MnI_2$ (18.5 mg) so that a molar ratio between Pb and Mn is 95:5. For Compound No. 1-3, a mixed metal iodide solution was prepared by mixing $PbI_2$ (539.4 mg) with copper iodide (CuI) (5.7 mg) so that a molar ratio between Pb and Cu is 97.5:2.5. Compound No. 1-4 was prepared by mixing $PbI_2$ (525.5 mg) with CuI (11.4 mg) so that a molar ratio between Pb and Cu is 95:5. In addition, for Compound Nos. 1-5 and 1-6 using $CuBr_2$ rather than CuI as the metal precursor, a mixed metal iodine-bromide solution (Compound No. 1-5) was prepared by mixing $PbI_2$ (539.4 mg) with copper bromide ($CuBr_2$) (6.7 mg) so that a molar ratio between Pb and Cu is 97.5:2.5. Compound No. 1-6 was prepared by mixing $PbI_2$ (525.5 mg) with $CuBr_2$ (13.4 mg) so that a molar ratio between Pb and Cu is 95:5.

Further, Compound No. 1-7 using three metals of Pb, Mn and Cu together was prepared by mixing $PbI_2$ (525.5 mg), $MnI_2$ (9.3 mg), and CuI (5.7 mg) so that a molar ratio of each element (Pb:Mn:Cu) is 95:2.5:2.5. Compound No. 1-8 was prepared by mixing $PbI_2$ (511.8 mg), $MnI_2$ (9.3 mg), and CuI (11.4 mg) so that a molar ratio of each element (Pb:Mn:Cu) is 92.5:2.5:5.

Then, the previously prepared $CH_3NH_3I$ solution was mixed with each metal precursor solution so as to have the same number of moles as the total number of moles of metals of the metal precursor solution to thereby prepare mixed metal precursor solutions. The preparation process of the precursor solution was performed in a glove box filled with nitrogen.

Figure 3A:
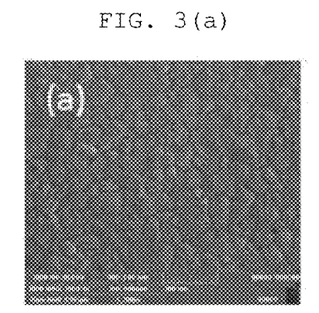
FIG. 3(a) is scanning electron microscope (SEM) image of photo-absorption layer film manufactured by compound No. 1-0 in Comparative Example 1.
Figure 3B:
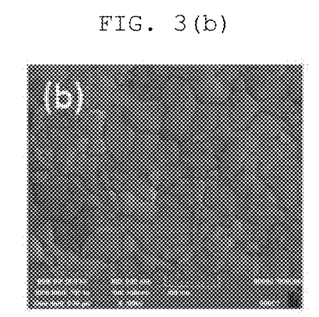
FIG. 3(b) is scanning electron microscope (SEM) image of photo-absorption layer film manufactured by compound No. 1-2 in Example 1.
Figure 3C:
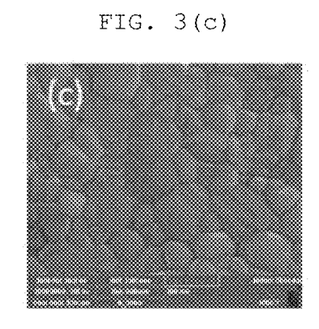
FIG. 3(c) is scanning electron microscope (SEM) image of photo-absorption layer film manufactured by compound No. 1-4 in Example 1.
Figure 4:
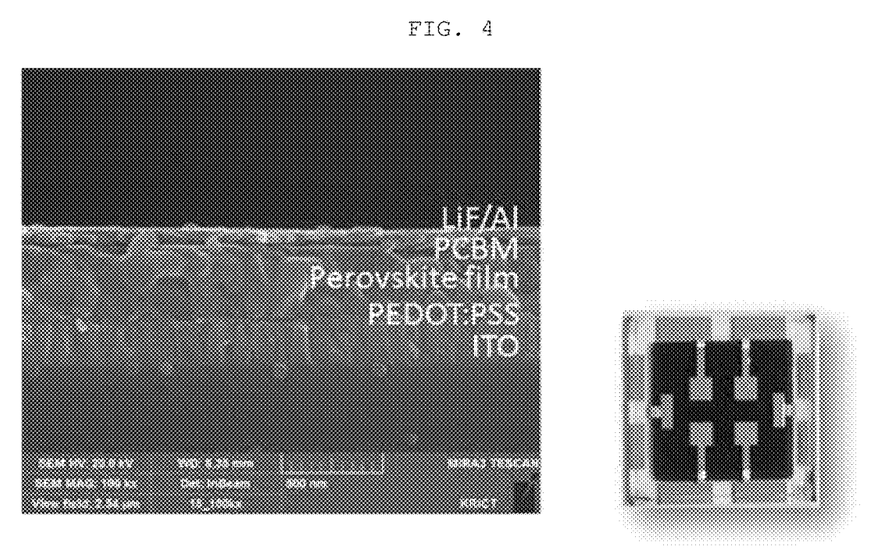
FIG. 4 shows a cross section and an appearance of a thin-film type photoelectric conversion device manufactured by Example of the present invention.

In order to manufacture the thin-film solar cell similar to the device shown in FIG. 1, a conductive transparent electrode was firstly prepared and a first charge transport layer was coated thereon. Specifically, pre-patterned ITO glass was sequentially soaked into neutral detergent, deionized water, acetone, and isopropanol solvent for 15 minutes, washed by using ultrasonic, and dried in the oven, followed by UV-ozone treatment. In order to form a hole transport layer (thickness of 40 to 50 nm) which is the first charge transport layer thereon, a PEDOT:PSS dispersion liquid (Clevios, AI4083) passing through a microfilter was spin coated for 1 minute at 3000 rpm, followed by heat treatment under air atmosphere (140° C., 30 minutes). Then, the previously prepared mixed metal precursor solution was dropped on a PEDOT:PSS layer within a glove box filled with nitrogen, and spin coated so that a photoactive layer film has a thickness of about 300 nm. After spin coating, the sample was placed on a hot plate at which a surface temperature was maintained at 110° C., and heat treated for 10 minutes. Scanning electron microscope (SEM) images of the surface of the finally heat treated photoactive layer thin-films were shown in FIG. 3(a) to FIG. 3(c). FIG. 3(a) is an image of Compound No. 1-0 which is Comparative Example 1, FIG. 3(b) is an image of Compound No. 1-2 in Example 1, and FIG. 3(c) is an image of Compound No. 1-4 in Example 1. It could be appreciated from FIG. 3(a) to FIG. 3(c) that when Mn and Cu are added, coarse crystal grain are formed, and in particular, when Cu is added, the photoactive layer is formed into significantly coarse crystal grain. After the photoactive layer thin film was formed, it was confirmed from X-ray diffraction analysis that a thin film having a single perovskite structure was formed. An electron transport layer as a second charge transport layer was spin coated on the photoactive layer thin film. C60-PCBM used in general organic thin-film solar cell was dissolved in chlorobenzene solvent to be 2 wt % or less, and the mixture was coated for 1 minute at about 1500 rpm. Then, LiF and Al were vacuum-deposited on the electron transport layer to thereby form a counter electrode of a thin film of LiF (~1 nm)/Al (~100 nm), thereby manufacturing a thin-film solar cell. Appearance and cross section of the completed representative solar cell were shown in FIG. 4.

Figure 5:
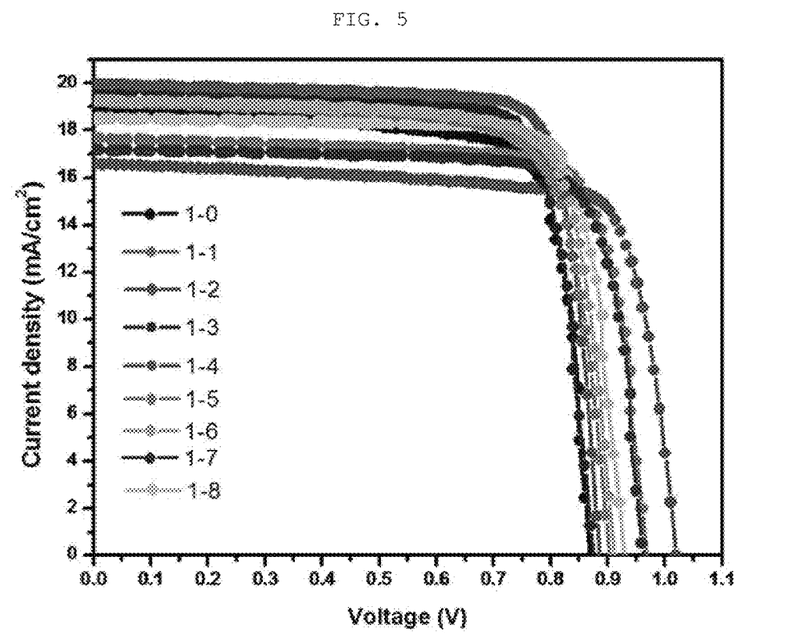
FIG. 5 shows graphs of performance of photoelectric conversion devices manufactured by Example 1 and Comparative Example 1 of the present invention.

Difference in performance measured at 1 sun, of the solar cells according to kinds of the photoactive layer thin films was summarized and shown in Table 1 and FIG. 5. As compared to the lead iodide ($PbI_2$) single-based solar cell generally served as the basic metal halide in this field which is shown as Comparative Example 1 below, all of the samples of the present invention had excellent performance properties. In general, Pb:Mn of mixed metal-based cell had 0.1V or more of increased open circuit voltage (Voc), Pb:Cu of mixed metal-based cell had similar open circuit voltage, but increased short-circuit current (Jsc) and fidelity (FF), and Pb:Mn:Cu of three components mixed metal-based cell had the best value in fidelity, and accordingly, these mixed metal-based cell generally had more excellent photoelectric conversion efficiency characteristic as compared to the single-based cell. As shown in Examples, the mixed solvent of DMSO/BLT had higher photoelectric conversion efficiency than that of DMSO single solvent, but this result was obtained without process optimization of the single solvent. Therefore, if the process optimization of the single solvent is performed, it is possible to increase the photoelectric conversion efficiency.

Figure 6:
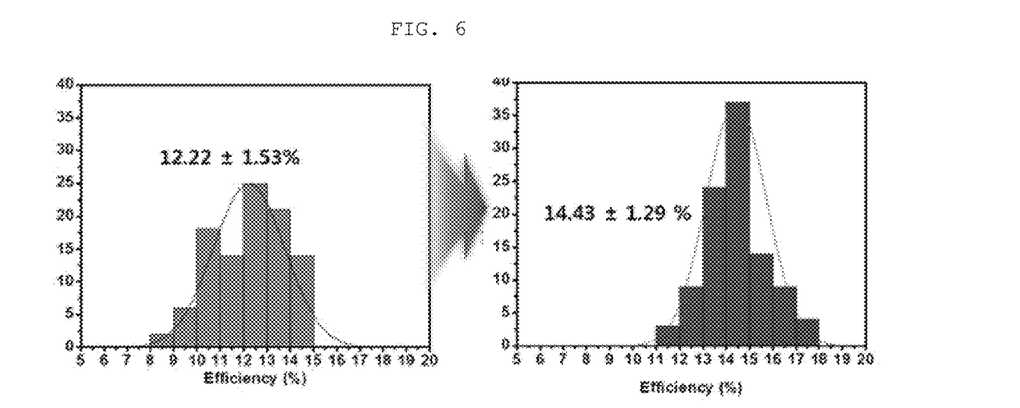
FIG. 6 shows device reproducibility which is cell efficiency distribution, measured according to the present invention.
Figure 7:
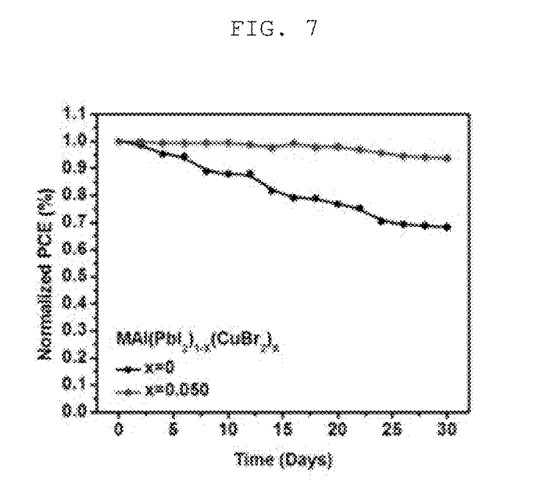
FIG. 7 shows device stability, measured according to the present invention.
Figure 8:
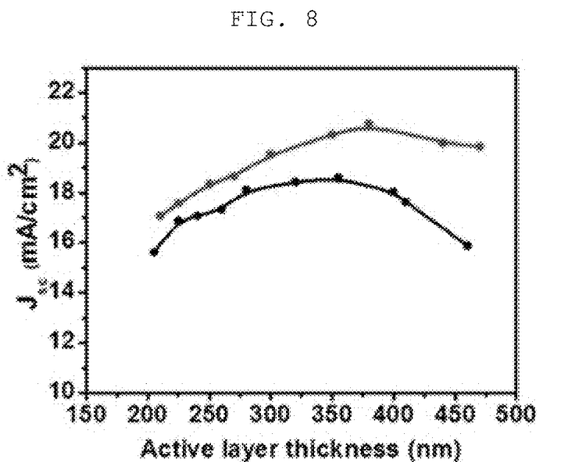
FIG. 8 shows current density depending on thickness of the photo-absorption layer, measured according to the present invention.

As described above, in the case of the photoactive layer containing copper (Cu), a size of a crystal may be remarkably increased, such that the photoactive layer may be formed of coarse crystal grain. In the case of the photoactive layer containing copper (Cu), it was confirmed that a copper doping level was produced on energy band gap, and hole density and conductivity were also largely increased. Further, in the case of the photoactive layer containing two kinds of halogen of I and Br together with Cu, it was confirmed that device stability and device reproducibility were remarkably increased. FIG. 6 shows efficiency distribution of a number of solar cells manufactured by the same method as Example 1 using Compound No. 1-6 (Right side), and for comparison, FIG. 6 also shows efficiency distribution of the existing solar cells manufactured by the same method as Example but using Compound No. 1-0 which is Comparative Example 1 (Left side). As shown in FIG. 6, as compared to the existing other organic-inorganic hybrid perovskite (for example: $CH_3NH_3PbI_3$)-based solar cell, it could be appreciated that the samples of the present invention had remarkably narrow distribution to provide excellent device reproducibility. FIG. 7 shows stability of a device manufactured by using Compound No. 1-6, and for comparison, FIG. 7 also shows stability of the existing solar cell manufactured by the same method as Example but using Compound No. 1-0 which is Comparative Example 1. As shown in FIG. 7, it could be appreciated that when continuously driving a cell at 1 sun for 30 days, cell efficiency was maintained to be 90% or more right after the manufacture. In addition, in the case of the photoactive layer containing two kinds of halogen of I and Br together with Cu, it was confirmed that recombination was effectively prevented in the photoactive layer. FIG. 8 shows current density for each thickness of the photoactive layer of the device manufactured by using Compound 1-6 and the existing solar cell manufactured by the same method as Example but using Compound No. 1-0. As shown in FIG. 8, it could be appreciated that in the case of the solar cell having the photoactive layer of the existing other organic-inorganic hybrid perovskite (for example: $CH_3NH_3PbI_3$), decrease in current due to recombination already occurred at a thickness of 450 nm. On the contrary, even though the photoactive layer containing two kinds of halogen of I and Br together with Cu had increased thickness, there was limitation in absorbing light, and the decrease in current due to recombination was not significant in the photoactive layer, such that the thickness was increased, and the current density was almost constantly saturated.

Comparative Example 1

Device was manufactured by the same method as Example 1 except for using lead iodide ($PbI_2$) single component as a metal halide component and performance thereof was measured (Compound No. 1-0).

TABLE 1

| | Compound No. | Composition $AMX_3$ | Voc (V) | Jsc (mA/cm$^2$) | FF (%) | PCE (%) |
|---|---|---|---|---|---|---|
| Example 1 | #1-1 | A = $CH_3NH_3$<br>M = Pb(0.975):Mn(0.025),<br>X = I | 0.97 | 17.66 | 79.05 | 13.55 |
| | #1-2 | A = $CH_3NH_3$<br>M = Pb(0.95):Mn(0.05)<br>X = I | 1.01 | 16.58 | 78.65 | 13.30 |
| | #1-3 | A = $CH_3NH_3$<br>M = Pb(0.975):Cu(0.025)<br>X = I | 0.87 | 19.34 | 77.55 | 13.02 |
| | #1-4 | A = $CH_3NH_3$<br>M = Pb(0.95):Cu(0.05)<br>X = I | 0.88 | 19.95 | 80.72 | 14.27 |
| | #1-5 | A = $CH_3NH_3$<br>M = Pb(0.975):Cu(0.025)<br>X = I(295/300):Br(5/300) | 0.90 | 19.24 | 75.72 | 13.15 |

TABLE 1-continued

| Compound No. | Composition AMX$_3$ | Voc (V) | Jsc (mA/cm$^2$) | FF (%) | PCE (%) |
|---|---|---|---|---|---|
| #1-6 | A = CH$_3$NH$_3$<br>M = Pb(0.95):Cu(0.05)<br>X = I(290/300):Br(10/300) | 0.91 | 19.22 | 78.18 | 13.68 |
| #1-7 | A = CH$_3$NH$_3$<br>M = Pb(0.95):Mn(0.25):<br>Cu(0.25), X = I | 0.96 | 17.22 | 79.39 | 13.18 |
| #1-8 | A = CH$_3$NH$_3$<br>M = Pb(0.925):Mn(0.25):<br>Cu(0.5), X = I | 0.93 | 18.48 | 81.05 | 13.90 |
| Comparative Example 1 #1-0 | A = CH$_3$NH$_3$<br>M = Pb, X = I | 0.87 | 19.01 | 77.05 | 12.73 |

EXAMPLE 2

Methyl ammonium bromide (CH$_3$NH$_3$Br) (134 mg) was dissolved in a mixed solvent of BTL and DMSO (volume ratio=6/4) (1 CC) to prepare a solution according to the same method as Example 1. In addition, to a separate mixed solvent of BTL and DMSO (volume ratio=6/4) (1 CC), tin iodide (SnI$_2$) (435.8 mg) and manganese iodide (MnI$_2$) (9.3 mg) were dissolved together to thereby prepare a mixed metal iodide solution in which a molar ratio between Sn and Cu is 97.5:2.5 (Compound No. 2-1 in Table 2).

Compound No. 2-2 was prepared by mixing SnI$_2$ (435.8 mg) with copper iodide (CuI) (5.7 mg) so that a molar ratio between Sn and Cu is 97.5:2.5. Finally, the previously prepared CH$_3$NH$_3$Br solution was mixed with each mixed metal halide solution at the same molar ratio to thereby prepare mixed metal precursor solutions. The preparation process of the precursor solution was performed in a glove box filled with nitrogen. The remaining process for manufacturing the solar cell was performed by the same method as Example 1. Similar to Example 1, after the photoactive layer was formed, it was confirmed from X-ray diffraction analysis that a thin film having a single perovskite phase was formed.

Figure 9:
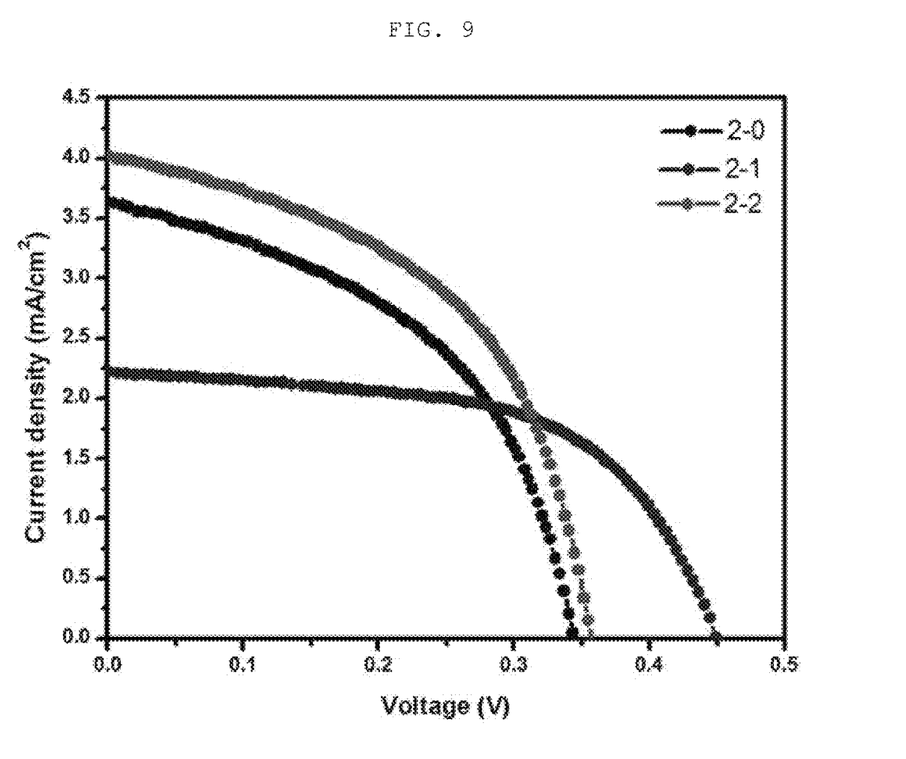
FIG. 9 shows graphs of performance of photoelectric conversion devices manufactured by Example 2 and Comparative Example 2 of the present invention.

The manufactured solar cell had high open circuit voltage (Voc), short-circuit current (Jsc) and fidelity (FF) as compared to a Sn single metal solar cell, thereby having high photoelectric conversion efficiency (see Example 2 in Table 2 and FIG. 9).

Comparative Example 2

Device was manufactured by the same method as Example 1 except for using tin iodide (SnI$_2$) single component as a metal halide component and performance thereof was measured at 1 sun (Compound No. 2-0 in Table 2).

EXAMPLE 3

A mixed metal iodine-bromide solution (Compound No. 3-1) was prepared by mixing lead iodide (PbI$_2$) (539.4 mg) with copper bromide (CuBr$_2$) (6.7 mg) in the mixed solvent of BTL and DMSO (volume ratio=6/4) (1 CC) so that a molar ratio between Pb and Cu is 97.5:2.5, like Compound Nos. 1-5 and 1-6 in Table 1, and Compound No. 3-2 was prepared by mixing PbI$_2$ (525.5 mg) with CuBr$_2$ (13.4 mg) so that a molar ratio between Pb and Cu is 95:5, according to the same method as Example 1.

Provided that when a thin-film having a single perovskite phase was formed, a two-step method was used unlike Example 1. In other words, at the time of spin coating of Compound Nos. 3-0, 3-1, and 3-2, the prepared mixed metal iodine-bromide solution was dropped in the center of spin coating, and then, non-polar solvent such as toluene or chlorobenzene was further dropped in the center of the spin coating, on the substrate on which the PEDOT:PSS layer was formed. After the perovskite thin-film was manufactured by the two-step method, the solar cell was manufactured by the same method as Example 1. Similar to Examples 1 and 2, after the photoactive layer was formed, it was confirmed from X-ray diffraction analysis that a thin film having a single perovskite phase was formed.

Figure 10:
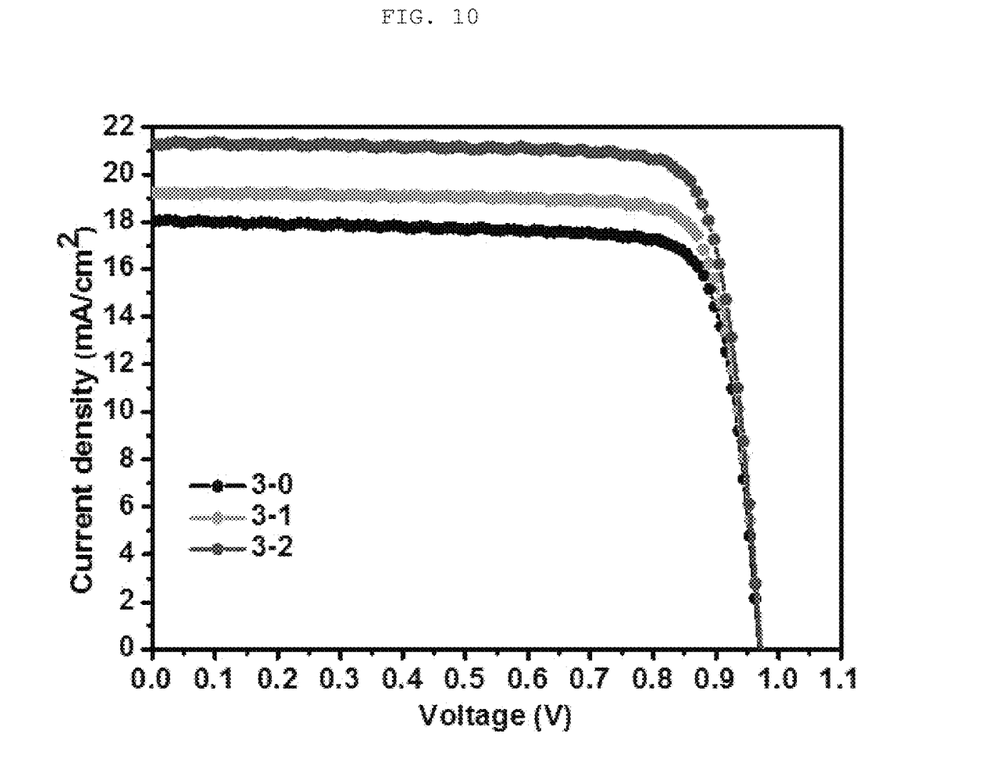
FIG. 10 shows graphs of performance of photoelectric conversion devices manufactured by Example 3 and Comparative Example 3 of the present invention.

Table 3 shows properties (at 1 sun) of the solar cells manufactured by Example 3, and FIG. 10 shows graphs of performance of the solar cell manufactured by Example 3. As shown in Table 3 and FIG. 10, the manufactured solar cell had high short-circuit current (Jsc) and fidelity (FF) as compared to a Pb single metal solar cell, thereby having high photoelectric conversion efficiency.

Comparative Example 3

Device was manufactured by the same method as Example 3 except for using lead iodide (PbI$_2$) single com-

TABLE 2

| | Compound No. | Composition AMX$_3$ | Voc (V) | Jsc (mA/cm$^2$) | FF (%) | PCE (%) |
|---|---|---|---|---|---|---|
| Example 2 | #2-1 | A = CH$_3$NH$_3$<br>M = Sn(0.95):Mn(0.025)<br>X = I(2/3):Br(1/3) | 0.43 | 2.21 | 61.74 | 0.59 |
| | #2-2 | A = CH$_3$NH$_3$<br>M = Sn(0.95):Cu(0.025)<br>X = I(2/3):Br(1/3) | 0.35 | 4.02 | 50.79 | 0.73 |
| Comparative Example 2 | #2-0 | A = CH$_3$NH$_3$<br>M = Sn, X = I(2/3):Br(1/3) | 0.34 | 3.64 | 46.04 | 0.56 | ponent as a metal halide component and performance thereof was measured (Compound No. 3-0).

TABLE 3

| | Compound No. | Composition AMX$_3$ | VOC (V) | JSC (mA/cm$^2$) | FF (%) | PCE (%) |
|---|---|---|---|---|---|---|
| Example 3 | #3-1 | A = CH$_3$NH$_3$<br>M = Pb(0.975):Cu(0.025)<br>X = I(295/300):Br(5/300) | 0.97 | 19.21 | 81.92 | 15.32 |
| | #3-2 | A = CH$_3$NH$_3$<br>M = Pb(0.95):Cu(0.05)<br>X = I(290/300):Br(10/300) | 0.97 | 21.31 | 82.13 | 17.00 |
| Comparative Example 3 | #3-0 | A = CH$_3$NH$_3$<br>M = Pb, X = I | 0.96 | 17.98 | 81.32 | 14.17 |

EXAMPLE 4

A solar cell was manufactured by the same method as Example 1 except for preparing a mixed metal precursor solution by mixing lead iodide (PbI$_2$) with copper iodide (CuI$_2$) so as to satisfy the composition of Compound 1-4 in Table 1 in DMF solvent rather than the mixed solvent of BTL and DMSO, or by mixing lead iodide (PbI$_2$) with copper bromide (CuBr$_2$) so as to satisfy the composition of Compound 1-6 in Table 1 in the DMF solvent rather than the mixed solvent of BTL and DMSO. In Table 4, Compound 4-1 showed results of the solar cell in which the photo-absorption layer of CH$_3$NH$_3$Pb$_{0.95}$Cu$_{0.05}$I$_3$ was formed in Example 4, and Compound 4-2 showed results of the solar cell in which the photo-absorption layer of CH$_3$NH$_3$Pb$_{0.95}$Cu$_{0.05}$I$_{2.9}$Br$_{0.1}$ was formed in Example 4.

Table 4 shows properties (at 1 sun) of the solar cells manufactured by Example 4. The manufactured solar cell had high short-circuit current (Jsc) and fidelity (FF) as compared to the Pb single metal solar cell, thereby having high photoelectric conversion efficiency.

Comparative Example 4

Device was manufactured by the same method as Example 4 except for using lead iodide (PbI$_2$) single component as a metal halide component and performance thereof was measured (Compound No. 4-0).

TABLE 4

| | Compound No. | Composition AMX$_3$ | Voc (V) | Jsc (mA/cm$^2$) | FF (%) | PCE (%) |
|---|---|---|---|---|---|---|
| Example 4 | 4-1 | A = CH$_3$NH$_3$<br>M = Pb (0.95):Cu (0.05)<br>X = I | 0.90 | 14.44 | 76.53 | 9.95 |
| | 4-2 | A = CH$_3$NH$_3$<br>M = Pb (0.95):Cu (0.05)<br>X = I (290/300):Br (10/300) | 0.88 | 15.56 | 76.91 | 10.54 |
| Comparative Example 4 | 4-0 | A = CH$_3$NH$_3$<br>M = Pb,<br>X = I | 0.91 | 11.60 | 75.76 | 8.06 |

The mixed metal halide perovskite compound according to the present invention may have remarkably excellent photoelectric conversion efficiency as compared to a perovskite compound including an organic cation, a single metal cation and a halogen anion or a perovskite compound including an organic cation, a mixed metal cation except for the mixed metal cation of the present invention and a halogen anion, and the mixed metal halide perovskite compound according to the present invention may form the thin film having a dense and large crystal.

In addition, the mixed metal halide perovskite compound according to the present invention may have photovoltaic stability, and may have remarkably excellent reproducibility of performance of a device manufactured from the mixed metal halide perovskite compound to have excellent commercial viability, and may prevent photocurrent extinction due to recombination, thereby being implemented into a thick layer.

Further, the mixed metal halide perovskite compound according to the present invention may have an excellent effect in absorbing light even at a long wavelength.

Hereinabove, although the present invention is described by specific matters, limited exemplary embodiments, and drawings, they are provided only for assisting in the entire understanding of the present invention. Therefore, the present invention is not limited to the exemplary embodiments. Various modifications and changes may be made by those skilled in the art to which the present invention pertains from this description.

Therefore, the spirit of the present invention should not be limited to the above-described exemplary embodiments, and the following claims as well as all modified equally or equivalently to the claims are intended to fall within the scopes and spirit of the invention.

What is claimed is:

1. A mixed metal halide perovskite compound represented by Chemical Formula 1 below:

$$AM^1_xM^2_yX_3 \qquad \text{Chemical Formula 1}$$

in Chemical Formula 1, A is a monovalent organic cation, M$^1$ is a first metal cation selected from Pb or Sn, M$^2$ is a second metal cation including at least one selected from Cu and Mn, X is one or two or more kinds of halogen anions selected from F, Cl, Br and I, a molar ratio of M$^1$ and M$^2$ satisfies x+y=1, and x is a real number of 0.9 to 0.98, and wherein two or more kinds of metal cation including the first metal cation and the second metal cation are selected from i) to v) below:
  i) Pb and Mn,
  ii) Pb and Cu,
  iii) Sn and Mn,
  iv) Sn and Cu, and
  v) Pb, Mn and Cu.

2. The mixed metal halide perovskite compound of claim 1, wherein when M$^2$ is a mixture of Cu and Mn, each content of Cu and Mn is a real number of 0.001 to 0.099, and the sum of contents of Cu and Mn has a molar ratio of 0.02 to 0.1.

3. The mixed metal halide perovskite compound of claim 1, wherein the halogen anion includes bromine ions and iodine ions.

4. A photoelectric conversion device comprising the mixed metal halide perovskite compound of claim 1 as a photoactive material.

5. The photoelectric conversion device of claim 4, wherein the photoelectric conversion device includes a transparent electrode, a first charge transport layer formed on the transparent electrode, a photoactive layer formed on the first charge transport layer and containing the mixed metal halide perovskite compound, a second charge transport layer formed on the photoactive layer, and a counter electrode formed on the second charge transport layer.

* * * * *